(12) United States Patent
Bothe et al.

(10) Patent No.: US 7,199,115 B2
(45) Date of Patent: Apr. 3, 2007

(54) 17α-FLUOROSTEROIDS, PHARMACEUTICAL COMPOSITIONS CONTAINING 17α-FLUOROSTEROIDS AND A METHOD OF MAKING THEM

(75) Inventors: Ulrich Bothe, Berlin (DE); Peter Droescher, Weimar (DE); Walter Elger, Berlin (DE); Gudrun Reddersen, Jena (DE); Bernd Menzenbach, Jena (DE); Hans-Udo Schweikert, Bonn (DE); Alexander Hillisch, Velbert (DE); Birgitt Schneider, Jena (DE)

(73) Assignee: Schering AG, Berlin (DE)

( * ) Notice: Subject to any disclaimer, the term of this patent is extended or adjusted under 35 U.S.C. 154(b) by 47 days.

(21) Appl. No.: 11/104,736

(22) Filed: Apr. 13, 2005

(65) Prior Publication Data

US 2005/0234027 A1    Oct. 20, 2005

Related U.S. Application Data

(60) Provisional application No. 60/563,491, filed on Apr. 19, 2004.

(51) Int. Cl.
*A61K 31/56* (2006.01)
*C07J 3/00* (2006.01)

(52) U.S. Cl. .................................. 514/177; 552/611
(58) Field of Classification Search ............... 552/611; 514/177
See application file for complete search history.

(56) References Cited

U.S. PATENT DOCUMENTS 3,112,305 A    11/1963    Kirk et al.
3,118,882 A    1/1964    Deghenghi

FOREIGN PATENT DOCUMENTS

CA    2 421 302 A1    3/2003
DE    195 35 572        3/1996
DE    100 43 846 A1    4/2002

OTHER PUBLICATIONS

Turuta, A.M. et al: "Transformed Steroids. 180 . . . " Izvestiya Akademia Nauk SSSR, Seriya Khimicheskaya, 1990, (3), pp. 595-601.
Reichert W., et al: "Stable Expression of Human . . . " Journal of Steroid Biochemistry and Molecular Biology, BD. 78, NR. 3, Sep. 2001, pp. 275-284.
Hartmann, R., et al: "Synthesis and Evaluation of Novel . . . " Journal of Medicinal Chemistry, BD. 43, NR. 22, Nov. 2, 2000. pp. 4266-4277.
Petrow, V., et al: "Prostatic Cancer . . . " Journal of Steroid Biochemistry, BD. 19, NR. 4, 1983, pp. 1491-1502.
Petrow, V., et al: "Prostate III A Structural . . . " Journal of Steroid Biochemistry, BD. 32, NR. 3, 1989, pp. 399-408.

*Primary Examiner*—Barbara P. Badio
(74) *Attorney, Agent, or Firm*—Michael J. Striker

(57) ABSTRACT

New 17α-fluorosteroid compounds of formula (I) are disclosed:

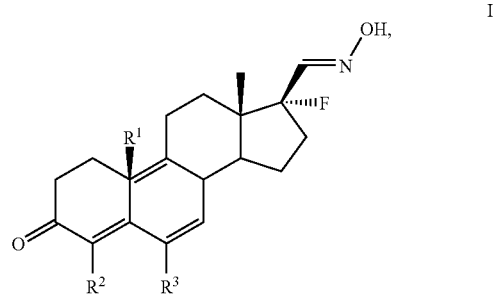

wherein $R^1$ denotes H or methyl; $R^2$ and $R^3$ each denote H, Cl or methyl; and either a double bond or a single bond is present between C-6 and C-7 and also C-9 and C-10 of the steroid ring system respectively. These compounds have an activity profile with hybrid character so that they act as inhibitors for 5α-reductase and as high potency gestagens. Pharmaceutical compositions containing them are disclosed. They are suitable for treatment of conditions, which are caused by high levels of androgen in organs and tissues. These new compounds can be used in combination with other hormonal substances, such as estrogens, testosterone and other androgens, as contraceptives and for other applications.

8 Claims, No Drawings

17α-FLUOROSTEROIDS, PHARMACEUTICAL COMPOSITIONS CONTAINING 17α-FLUOROSTEROIDS AND A METHOD OF MAKING THEM

CROSS-REFERENCE

U.S. Provisional Patent Application 60/563,491, filed Apr. 19, 2004, describes the invention described hereinabove and claimed in the claims appended hereinbelow and provides the basis for a claim of priority for the instant invention under 35 U.S.C. 119(e).

BACKGROUND OF THE INVENTION

The present invention concerns new 17α-fluorosteroid compounds, a method of making them and pharmaceutical compositions containing these compounds. The compounds according to the invention have an action profile with hybrid character so that they act as inhibitors of 5α-reductase and simultaneously as gestagens. They are suitable for treatment of illnesses or conditions, which are caused by elevated androgen levels in certain organs and tissues in men and women, e.g. acne, hirsutism, alopecia (male type), BPH and prostate carcinoma. The compounds according to the invention are suitable as contraceptives for women and for men, in combination with other hormonal substances, such as estrogens, testosterone and/or a powerful androgen.

17-chloromethylene steroid compounds, which indeed inhibit 5α-reductase, are known from the patent literature, namely DE 100 43 846.6. However these latter compounds are only weak gestagens in comparison to natural progesterone, as has been clearly demonstrated with the aid of tests for pregnancy maintenance with these compounds.

SUMMARY OF THE INVENTION

It is an object of the present invention to provide compounds, which have a more extensive or comprehensive action profile than those known in the prior art.

It is also an object of the present invention to provide new steroid compounds, especially new fluorinated steroid compounds, and a method to make them.

It is an additional object of the present invention to provide new steroid compounds and pharmaceutical compositions containing them for treating illnesses or conditions caused by elevated androgen levels in certain organs and tissues in men and women.

According to the invention these objects, and others which will be made more apparent hereinafter, are attained by the following 17α-fluorosteroid compounds of formula (I):

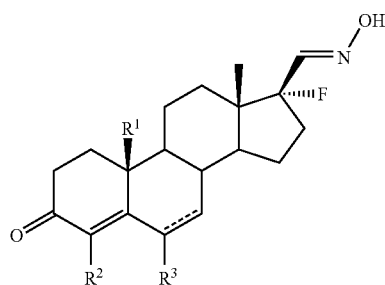

I wherein $R^1$ denotes a hydrogen atom or a methyl group;
$R^2$ and $R^3$ each denote, independently of each other, a hydrogen atom, a chlorine atom or a methyl group; and
wherein either a double bond or a single bond is present between carbon atom 6 and 7 of the steroid ring system; and also
wherein a single bond is present between carbon atoms 9 and 10 of the steroid ring system.

The 17α-fluorosteroid compound consisting of (E)-17α-fluoro-3-oxo-estra-4-en-17β-carbaldehyde oxime of formula (II):

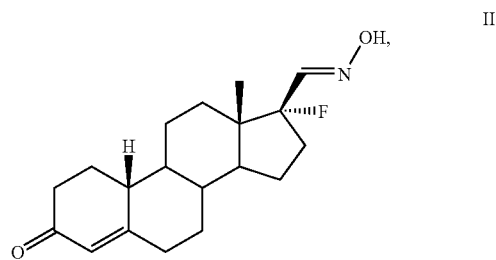

II is an especially preferred embodiment of formula I.

Suitable pharmaceutical compositions and preparations containing the compounds according to the invention of formula I can be made. These drugs contain the 17α-fluorosteroid compounds of formula I as effective ingredients, if necessary, together in a mixture with at least one other pharmacological and/or pharmaceutical active ingredient.

The use of the 17α-fluorosteroid compounds according to the invention to make a drug or medicine for treating prostate conditions or illnesses, alopecia of the male type, acne and hirsutism, for contraception in men and women and/or for inhibition of 5α-reductase and for treatment of cancerous conditions, which are unsatisfactorily affected by androgens, for example, prostate carcinoma.

The advantages obtained with the invention include especially that new 17α-fluorosteroid compounds were found that have a structure so that they surprisingly act as significant inhibitors of 5α-reductase and also as high potency gestagens.

The compounds according to the invention are suitable as a result of their action profile with hybrid character for treatment of illnesses and conditions, which are due to an elevated androgen level in certain organs and tissues in men and women, such as acne, hirsutism, alopecia (male type), BPH and prostate carcinoma. In women an increased level or concentration of 5α-dihydro-progesterone can contribute to serious disruption of conditions in premenstrual syndrome. This can be beneficially influenced by inhibition of 5α-reductase.

The simultaneous presence of gestagen activity in the compounds according to the invention leads to inhibition of gonad function in males and females. This effect is then desired when anti-fertility action or also inhibition of hormone secretions of the gonads should be achieved with the treatment. This is frequently the case with conditions of the prostate, such as benign prostate hyperplasia (BPH). Possible indications besides prostate conditions are contraception in both sexes, alopecia of the male type, acne and hirsutism and the treatment of cancerous conditions, which are undesirably influenced by androgens. The compounds according to the invention are used together with other hormonal substances, such as estrogens, testosterone and/or a powerful androgen, as a contraceptive for women and/or for men. In the latter application the action of testosterone in the prostate is reduced by inhibition of 5α-reductase, while the gestagen activity in the male gonads increases, which means that the spermatogenesis inhibition increases.

If the compounds according to the invention are used for female contraception, they can be used alone or in combination with an estrogen. All estrogen compounds are basically suitable for this purpose. Estrogens, which can be used, are for example ethinyl estradiol, 17β-estradiol and its esters, such as estradiol-3-benzoate, estradiol-17-valerate, estradiol-17-cypionoate, estradiol-17-undecylate, estradiol-17-enanthate and/or other estradiol esters and conjugate estrogens and pro-drugs of estradiol and other natural estrogens, such as estradiol-3-sulfamate.

When the compounds according to the invention are used for male contraception, they can be used alone or in combination with an androgen, such as e.g. testosterone and testosterone esters.

The medicines or drugs containing the compounds according to the invention are made in a known manner. The known and conventional pharmaceutical auxiliary and carrier substances for pharmaceutical, cosmetic and similar fields, which are described in the literature, can be employed.

The compounds according to the invention can be administered orally as capsules, pills, tablets, dragées, etc. or parenterally, for example, intra-peritoneally, intramuscularly, subcutanceously or percutaneously. The compounds can also be implanted in the tissues.

The dosage unit can contain a pharmaceutically compatible carrier, such as starch, sugar, sorbital, gelatins, lubricants, silica, talcum, etc. besides the effective ingredient.

The effective ingredient can be dissolved or suspended in a physiologically compatible dilution agent for parenteral administration. Very frequently oils are used as dilution agents with or without addition of a solvating agent, a surfactant, a suspension agent or an emulsifying agent. For example the oils used include olive oil, peanut oil, cotton seed oil, soy bean oil, castor oil and sesame seed oil.

The 17α-fluorosteroid compounds of formula I may also be used in the form of a sustained-release injection or an implant preparation, which can be formulated so that a delayed effective agent release takes place.

The implants can contain an inert material, for example a biodegradable polymer or synthetic silicones, such as silicone rubber. The effective ingredient can be incorporated for example in a patch for percutaneous application.

Different polymers, such as silicone polymers, ethylene vinyl acetate, polyethylene or polypropylene, are suitable for making intravaginal (e.g. vaginal rings) or intrauterine systems for local administration (such as, a pessary, a spiral, an IUD) loaded with the compounds according to the invention.

In order to attain improved bioavailability of the effective ingredient the compounds of formula I can also be formulated as cyclodextrine clathrates. The compounds of formula I are reacted with α,β- or γ-cyclodextrine or its derivatives for this purpose.

The compounds according to formula I can also be encapsulated with liposomes according to the invention.

Also the use of 17α-fluorosteroid compounds of formula I as a therapeutic active ingredient, especially for treatment of prostate conditions, alopecia of the male type, acne and hirsutism, for contraception in men and women and for inhibition of 5α-reductase and for treatment of cancerous conditions, which can be undesirably influenced by androgens, i.e. made worse by androgens, e.g. prostate carcinoma, is also part of the present invention.

Subsequently experimental data for progesterone receptor binding, 5α-reductase-type-2 activity in genital skin homogenates and in vivo data in the case of the exemplary compound of the invention, (E)-17α-fluoro-3-oxo-estra-4-en-17β-carbaldehyde oxime, are reported here.

The following examples illustrate the above-described invention in more detail, but the details in these examples should not be considered as limiting the claims appended hereinbelow.

EXAMPLES

Binding of Compound I to Progesterone Receptor

Biological material: Uterus cytosol, rabbit, pressed
Tracer: $^3$H—ORG 2058/Incubation conditions, 0–4° C.; 18 h
Reference substance: Progesterone=100%
Relative Binding affinity RBA [%]: 131±9%

5α-reductase-Type-2 Activity
Under optimum conditions at pH=5.5 in genital skin homogenates:
Compound 7 (in the synthesis scheme below): $IC_{50}$=245 nM.

PR-B Antagonisms and Agonisms
Antagonism $IC_{50}$ (mol/L)=3.39×10$^{-10}$
Agonism $IC_{50}$ (mol/L)=2.5×10$^{-10}$ In Vivo Data
Gestagen Activity in Pregnancy Maintenance Test
Mouse

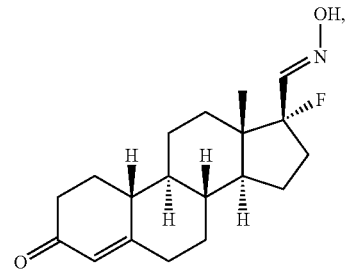

| Dosage Mg/animal/day | Rate of Maintained Gravidity |
|---|---|
| 0.003 | 0/3 |
| 0.03 | 2/2 |
| 0.3 | 3/3 |

The above data provide evidence of the activity profile with hybrid character of the compounds of formula I according to the invention, which inhibit 5α-reductase and act as gestagens.

The production and physical properties of the 17α-fluorosteroid compounds of formula I are illustrated, for example, by the following synthesis of the especially preferred compound, (E)-17α-fluoro-3-oxo-estra-4-en-17β-carbaldehyde oxime.

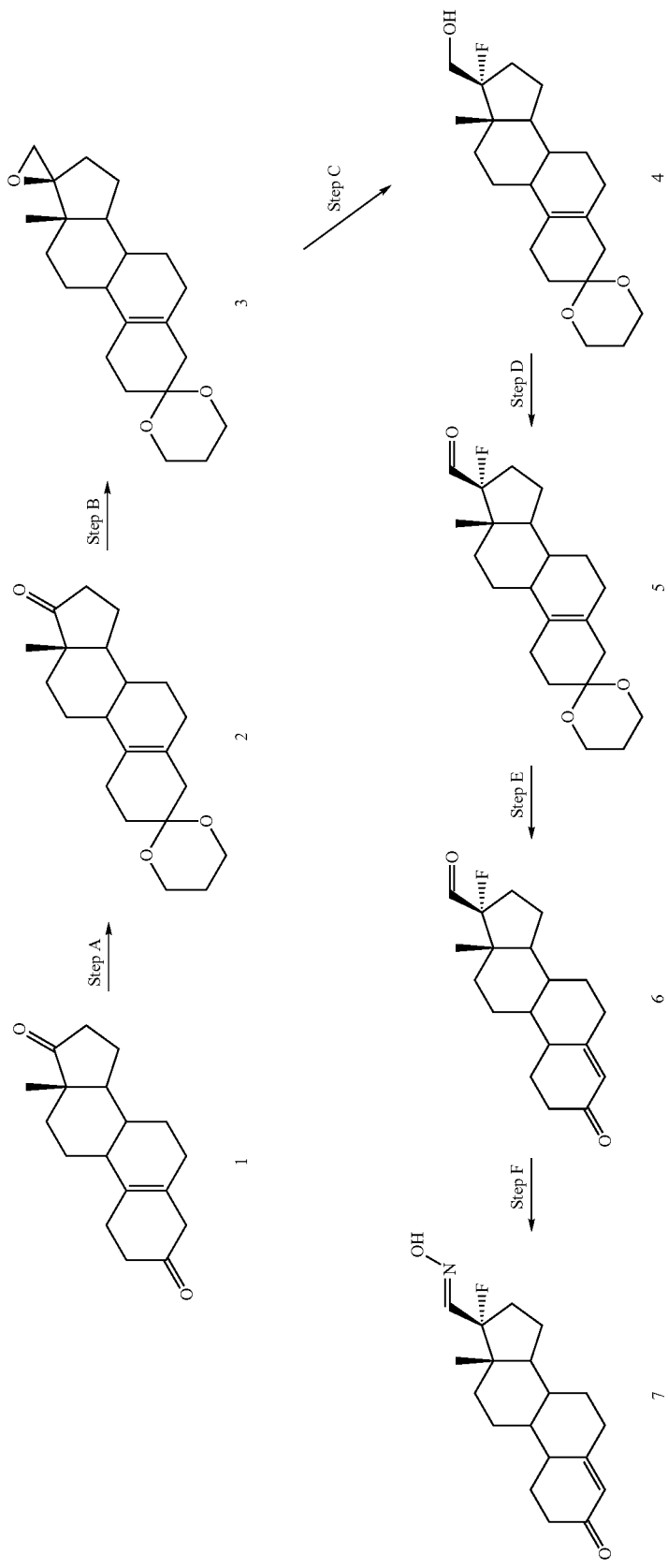

Synthesis of (E)-17α-fluoro-3-oxo-estra-4-en-17β-carbaldehyde oxime

Step A:

A mixture of estra-5(10)-en-3,17-dione (CAS number 3962-66-1, 15.1 g) (1) and pyridinium toluene-4-sulfonate PPTS (1.57 g) in 1,3-propandiol (200 ml) is stirred for 20 h at room temperature under argon. After that the mixture is poured into an aqueous $NaHCO_3$ saturated solution and the solid precipitate is separated by suction filtration. The solid is mixed twice with toluene and the toluene is removed by rotary evaporation. After drying in vacuum one obtains: 3-(1',3'-dioxan-2'-yl)-estra-5(10)-en-17-one (2) as a solid.

1H-NMR (400 MHz, $CDCl_3$, selected data): δ=0.88 (s,3H,Me), 2.28–2.38 (m, 2H), 2.46 (dd, J=9.1, 7.8 Hz, 1H), 3.8–4.1 (m, 4H, $OCH_2CH_2CH_2O$).

Step B:

A solution of the compound (2) from step A (15.0 g) in dimethylformamide (180 ml) is cooled with an ice bath and potassium-tert-butyl alcoholate (KOtBu, 10.9 g) is added portion-wise. The ice-cold mixture is stirred under argon for 2 h, poured into an aqueous saturated $NH_4Cl$ solution and extracted with ethyl acetate. After that it is washed with water and a saturated sodium chloride solution and then dried over sodium sulfate. After concentrating in a rotary evaporator (17S)-spiro-3-(1',3'-dioxan-2'-yl)-estra-5(10)-en-17,2'-oxirane (3) is obtained as a crude product (mixture of fine crystals and water, 16.2 g), which is further reacted without further purification.

Analytical data for the crude product (3):

1H-NMR (400 MHz, $CDCl_3$): δ=0.89 (s,3H,Me), 2.61 (d, J=5.1 Hz, 1H, C20H (a)), 2.92 (d, J=5.1 Hz, 1H, C20H (b)), 3.87–4.06 (m, 4H, $OCH_2CH_2CH_2O$).

Step C:

The crystal mixture is introduced into diisopropylethylamine (Hünig base, 80 ml) and N-ethyldiisopropylamine-tris-hydrofluoride (50 ml) is added. After 20 minutes heating under reflux conditions, additional diisopropylethylamine (50 ml) is added and the mixture is heated under reflux. After that it is cooled to room temperature, the reaction mixture is carefully poured into ice-cold aqueous saturated sodium bicarbonate solution and extracted with dichloromethane. The organic phase is washed with water and saturated sodium chloride solution and then concentrated. After column chromatographic purification on a silica gel column a mixed fraction (3.0 g) of 3-(1',3'-dioxan-2'-yl)-17α-fluoro-17β-hydroxymethylestra-4-ene (lesser yield product, 4) and 3-(1',3'-dioxan-2'-yl)-17β-fluoromethyl-17α-hydoxyestra-4-ene (main product) and other not identified ingredients is obtained.

19F-NMR (376 MHz, $CDCl_3$): δ=−223.1 (t, J=49 Hz, $CH_2F$, main product); −162--161.8 (m, C-17 Fluoro atom, lesser yield product 4).

Step D:

The mixed fraction from step C is dissolved in dichloromethane (35 ml) and Dess-Martin periodinane (1,1-dihydro-1,1,1-triacetoxy-1,2-benziodoxol-3(1H)-one, 1.43 g) is added under argon. After 75 minutes of stirring at room temperature, the resulting mixture is washed with 10% aqueous sodium thiosulfate solution, saturated sodium bicarbonate solution and saturated sodium chloride solution. After drying over sodium sulfate this mixture is concentrated in a rotary evaporator and purified by column chromatography on silica gel (eluent toluene/ethyl acetate 15:1). A viscous foam (729 mg) of the 3-(1',3'-dioxan-2'-yl)-17α-fluoroestra-4-en-17β-carbaldehyde (5) is obtained as the main product.

1H-NMR (400 MHz, $CDCl_3$, selected data): δ=0.77 (s, 3H, Me), 3.87–4.04 (m, 4H, $OCH_2CH_2CH_2O$), 9.77 (d, J(H,F)=6.3 Hz, 1H, CH=O); 19F-NMR (376 MHz, $CDCl_3$): δ=−164.1--163.9 (m, symmetric).

Step E:

A mixture of the foam (719 mg) from step D and p-toluene sulfonic acid hydrate (230 mg) in acetone (12 ml) is stirred for 5 hr and 20 min at room temperature under argon, diluted with aqueous saturated $NaHCO_3$ solution, extracted with ethyl acetate, washed with saturated common salt solution (aq. NaCl) and dried over sodium sulfate. After a two-pass or two-time column chromatographic purification on silica gel 17α-fluoro-3-oxo-estra-4-en-17β-carbaldehyde (6) as crude product.

1H-NMR (400 MHz, $CDCl_3$, selected data): δ=5.84 (s, 1H, 4-H), 9.78 (d, J(H,F) =5.8 Hz, 1H, CHO).

Step F:

The crude product from step E (170 mg) is dissolved in dichloromethane (2 ml) and pyridine (0.5 ml) and cooled in an ice cold bath. Hydroxylamine hydrochloride (23.3 mg) is added and the ice cold solution is stirred 1 hour under argon. Water is added, and the resulting solution is washed with dichloromethane and twice with an aqueous hydrochloric acid solution (0.5 M). The aqueous phase is extracted with dichloromethane and the combined organic phases are washed with water and saturated sodium chloride solution. After drying over sodium sulfate the latter solutions are concentrated in a rotary evaporator and a foam product is obtained, which is purified by column chromatography on silica gel. After crystallization from cyclohexane/acetone (E)-17α-fluoro-3-oxo-estra-4-en-17β-carbaldehyde oxime (7) is obtained as a white solid (46 mg). $C_{19}H_{26}FNO_2$ (319.4).

1H-NMR (400 MHz, $CDCl_3$): δ=0.75 (s, 3H, Me), 1.2–2.6 (m, 20H), 5.84 (s, 1H, 4-H), 7.32 (br. s, 1H, N=OH), 7.51 (d, J=9.0 Hz, 1H, CH=N); 19F-NMR (376 MHz, $CDCl_3$): δ=−151.1--151.0 (m, symmetric).

While the invention has been illustrated and described as embodied in 17α-fluorosteroid compounds, pharmaceutical compositions containing 17α-fluorosteroid compounds and a method of making them, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:

1. A 17α-fluorosteroid compound of formula (I):

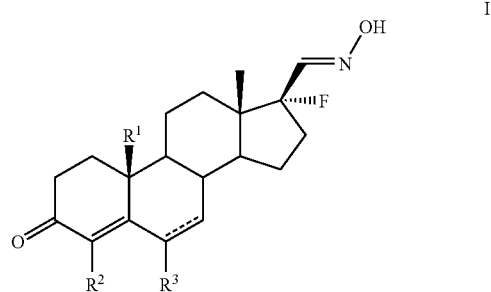

wherein $R^1$ denotes a hydrogen atom or a methyl group; $R^2$ and $R^3$ each denote, independently of each other, a hydrogen atom, a chlorine atom or a methyl group; and wherein either a double bond or a single bond is present between carbon atom 6 and 7 of a steroid ring system in the formula (I); and wherein a single bond is present between carbon atoms 9 and 10 of the steroid ring system.

2. The 17α-fluorosteroid compound as defined in claim 1, and consisting of (E)-17α-fluoro-3-oxo-estra-4-en-17β-carbaldehyde oxime of formula II:

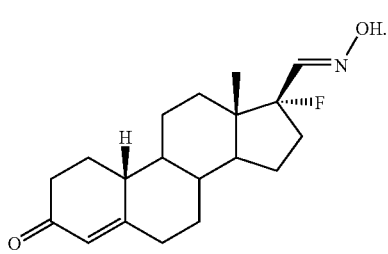

3. A pharmaceutical composition containing said 17α-fluorosteroid compound as defined in claim 1 and at least one member selected from the group consisting of pharmaceutical auxiliary agents and carrier substances.

4. The pharmaceutical composition as defined in claim 3, wherein said 17α-fluorosteroid compound is encapsulated in liposomes.

5. A pharmaceutical composition containing a cyclodextrine clathrate of said 17α-fluorosteroid compound as defined in claim 1 and at least one member selected from the group consisting of pharmaceutical auxiliary agents and carrier substances.

6. A method of treating at least one of prostate conditions, male-type alopecia, acne and hirsutism, said method administration of an effective amount of said 17α-fluorosteroid compound as defined in claim 1 to an individual having said at least one of said prostate conditions, male-type alopecia, acne and hirsutism.

7. A method of inhibition of 5α-reductase in an individual, said method comprising administering an effective amount of said 17α-fluorosteroid compound as defined in claim 1 to said individual.

8. A method of treating prostate cancer that is unfavorably influenced by androgens, said method administering an effective amount of said 17α-fluorosteroid compound as defined in claim 1 to an individual suffering from said prostate cancer.

* * * * *